US010514433B2

(12) United States Patent
Sakurai et al.

(10) Patent No.: US 10,514,433 B2
(45) Date of Patent: Dec. 24, 2019

(54) MAGNETIC RESONANCE IMAGING APPARATUS EXTRACTING AN INTERVERTEBRAL DISK REGION BASED ON SAGITTAL IMAGES OF A SUBJECT

(71) Applicant: TOSHIBA MEDICAL SYSTEMS CORPORATION, Otawara-shi (JP)

(72) Inventors: Yasuo Sakurai, Tochigi (JP); Kensuke Shinoda, Tochigi (JP); Yuichi Yamashita, Tochigi (JP)

(73) Assignee: TOSHIBA MEDICAL SYSTEMS CORPORATION, Otawara-Shi, Tochigi-ken (JP)

( * ) Notice: Subject to any disclaimer, the term of this patent is extended or adjusted under 35 U.S.C. 154(b) by 653 days.

(21) Appl. No.: 14/715,789

(22) Filed: May 19, 2015

(65) Prior Publication Data
US 2015/0260814 A1 Sep. 17, 2015

Related U.S. Application Data

(63) Continuation of application No. PCT/JP2013/081567, filed on Nov. 22, 2013.

(30) Foreign Application Priority Data

Nov. 22, 2012 (JP) ................................ 2012-256670

(51) Int. Cl.
G01R 33/483 (2006.01)
G01R 33/54 (2006.01)
(Continued)

(52) U.S. Cl.
CPC .......... G01R 33/4835 (2013.01); A61B 5/055 (2013.01); A61B 5/407 (2013.01);
(Continued)

(58) Field of Classification Search
USPC ........................ 324/300–322; 600/407–435; 382/128–131
See application file for complete search history.

(56) References Cited

U.S. PATENT DOCUMENTS 7,548,638 B2 6/2009 Graessner .................... 324/309
8,014,575 B2 * 9/2011 Weiss ...................... B60R 25/00
382/128

(Continued)

FOREIGN PATENT DOCUMENTS

CN 102090890 A 6/2011
JP 2003-210430 7/2003
(Continued)

OTHER PUBLICATIONS

Narasimhamurthy et al., "Automatic Derivation of Scan Plane Angles along with Vertebral Column of the Human Spine", *Proc. Intl. Soc. Mag. Reson. Med.* 19 (2011), May 13, 2011, p. 4534.

(Continued)

*Primary Examiner* — Melissa J Koval
*Assistant Examiner* — Tiffany A Fetzner
(74) *Attorney, Agent, or Firm* — Nixon & Vanderhye P.C.

(57) ABSTRACT

A magnetic resonance imaging apparatus according to an embodiment includes a processor and memory. The memory stores processor-executable instructions that, when executed by the processor, cause the processor to extract, based on a plurality of sagittal images at least including an intervertebral disk of a subject, an intervertebral disk region spanning across the plurality of sagittal images from spines visualized in the plurality of sagittal images; and set an imaging region of an intervertebral disk image based on the intervertebral disk region.

19 Claims, 8 Drawing Sheets

(51) Int. Cl.
  *G01R 33/56* (2006.01)
  *G01R 33/34* (2006.01)
  *G01R 33/48* (2006.01)
  *A61B 5/055* (2006.01)
  *A61B 5/00* (2006.01)

(52) U.S. Cl.
  CPC ... *G01R 33/34092* (2013.01); *G01R 33/4822* (2013.01); *G01R 33/543* (2013.01); *G01R 33/5608* (2013.01); *G01R 33/546* (2013.01)

(56) References Cited

U.S. PATENT DOCUMENTS

| | | | |
|---|---|---|---|
| 8,781,185 B2 | 7/2014 | Shinoda et al. | 382/128 |
| 9,280,718 B2 * | 3/2016 | Claude | A61B 5/055 |
| 9,693,706 B2 * | 7/2017 | Shiodera | A61B 5/055 |
| 2003/0139660 A1 | 7/2003 | Tatebayashi et al. | 324/309 |
| 2007/0173744 A1 | 7/2007 | Lai et al. | 324/309 |
| 2013/0230224 A1 * | 9/2013 | Claude | A61B 5/055 |
| | | | 382/131 |
| 2013/0289387 A1 * | 10/2013 | Shiodera | A61B 5/055 |
| | | | 600/419 |
| 2015/0077114 A1 * | 3/2015 | Shinoda | G01R 33/4833 |
| | | | 324/318 |
| 2015/0091569 A1 * | 4/2015 | Shinoda | A61B 5/055 |
| | | | 324/309 |
| 2015/0260814 A1 * | 9/2015 | Sakurai | A61B 5/055 |
| | | | 324/322 |
| 2016/0242673 A1 * | 8/2016 | Grychtol | A61B 5/0536 |
| 2019/0239926 A1 * | 8/2019 | Pavlovskaia | A61B 17/7013 |

FOREIGN PATENT DOCUMENTS

| | | |
|---|---|---|
| JP | 2005-237968 | 9/2005 |
| JP | 2012-45192 | 3/2012 |

OTHER PUBLICATIONS

International Search Report for PCT/JP2013/081567 dated Dec. 17, 2013, one page.
Chinese Office Action dated Dec. 29, 2016 in CN 201380056558.5.

* cited by examiner

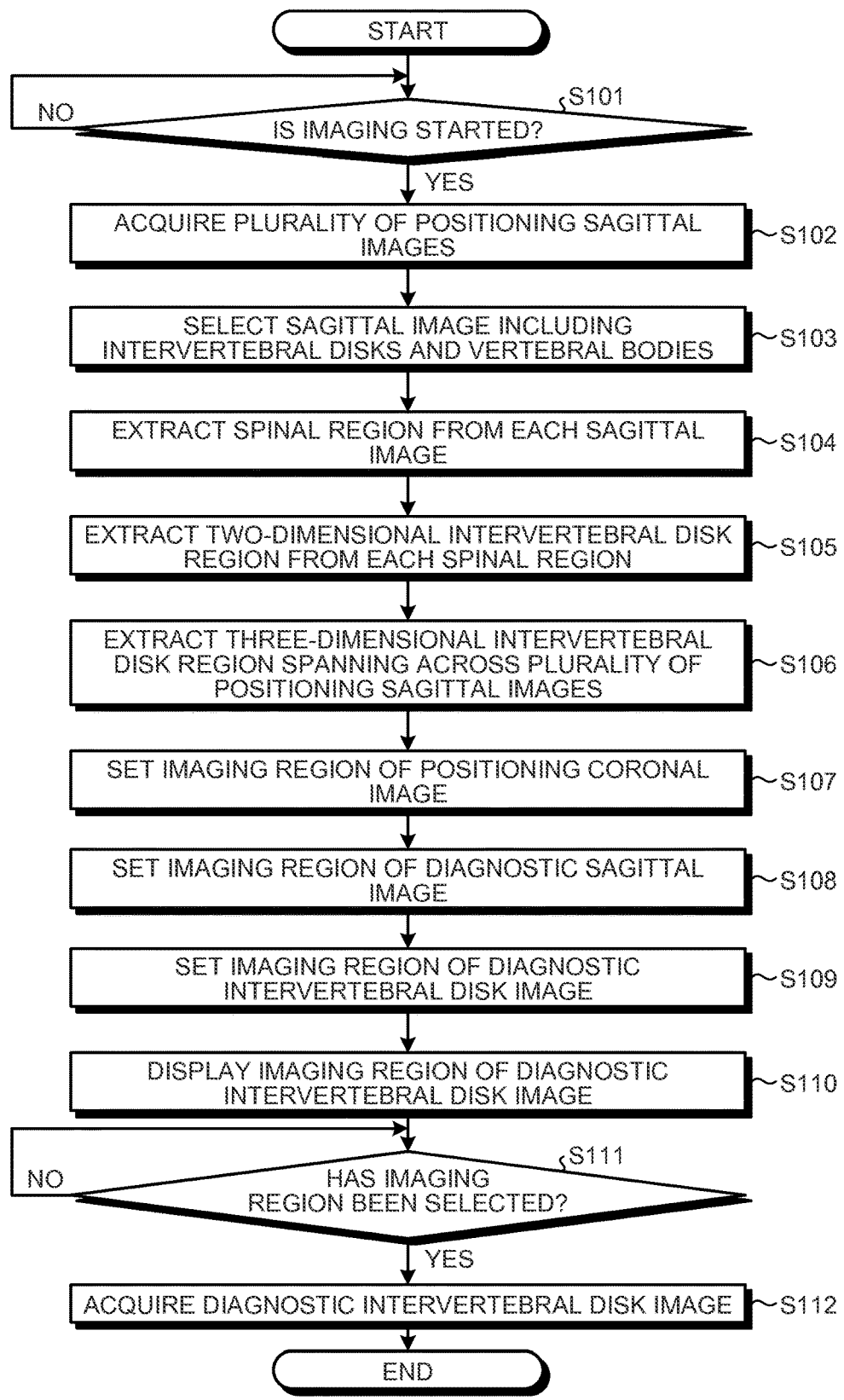

MAGNETIC RESONANCE IMAGING APPARATUS EXTRACTING AN INTERVERTEBRAL DISK REGION BASED ON SAGITTAL IMAGES OF A SUBJECT

CROSS-REFERENCE TO RELATED APPLICATIONS

This application is a continuation of PCT international application Ser. No. PCT/JP2013/081567 filed on Nov. 22, 2013 which designates the United States, incorporated herein by reference, and which claims the benefit of priority from Japanese Patent Application No. 2012-256670, filed on Nov. 22, 2012, the entire contents of which are incorporated herein by reference.

FIELD

Embodiments described herein relate generally to a magnetic resonance imaging apparatus.

BACKGROUND

Conventionally, in a diagnostic imaging examination of intervertebral disk injury using a magnetic resonance imaging apparatus, slice images parallel to intervertebral disks and including the intervertebral disks are acquired. Generally, in this diagnostic imaging examination, because it is unknown which of the intervertebral disks is ruptured, a plurality of intervertebral disks are imaged. Therefore, for example, there is a method of taking a positioning image (hereinafter, also "locator image") for confirming the position of an intervertebral disk so as to manually set an imaging region (hereinafter, also "imaging ROI (Region Of Interest)") including respective intervertebral disks on the positioning image by an operator.

BRIEF DESCRIPTION OF THE DRAWINGS

FIG. 9 is a flowchart of a process procedure for setting imaging regions performed by an MRI apparatus according to the embodiment.

DETAILED DESCRIPTION

A magnetic resonance imaging apparatus according to an embodiment includes a processor and memory. The memory stores processor-executable instructions that, when executed by the processor, cause the processor to extract, based on a plurality of sagittal images at least including an intervertebral disk of a subject, an intervertebral disk region spanning across the plurality of sagittal images from spines visualized in the plurality of sagittal images; and set an imaging region of an intervertebral disk image based on the intervertebral disk region.

Exemplary embodiments of a magnetic resonance imaging apparatus will be explained below in detail with reference to the accompanying drawings. In the following explanations, the magnetic resonance imaging apparatus is referred to as "MRI (Magnetic Resonance Imaging) apparatus".

Figure 1:
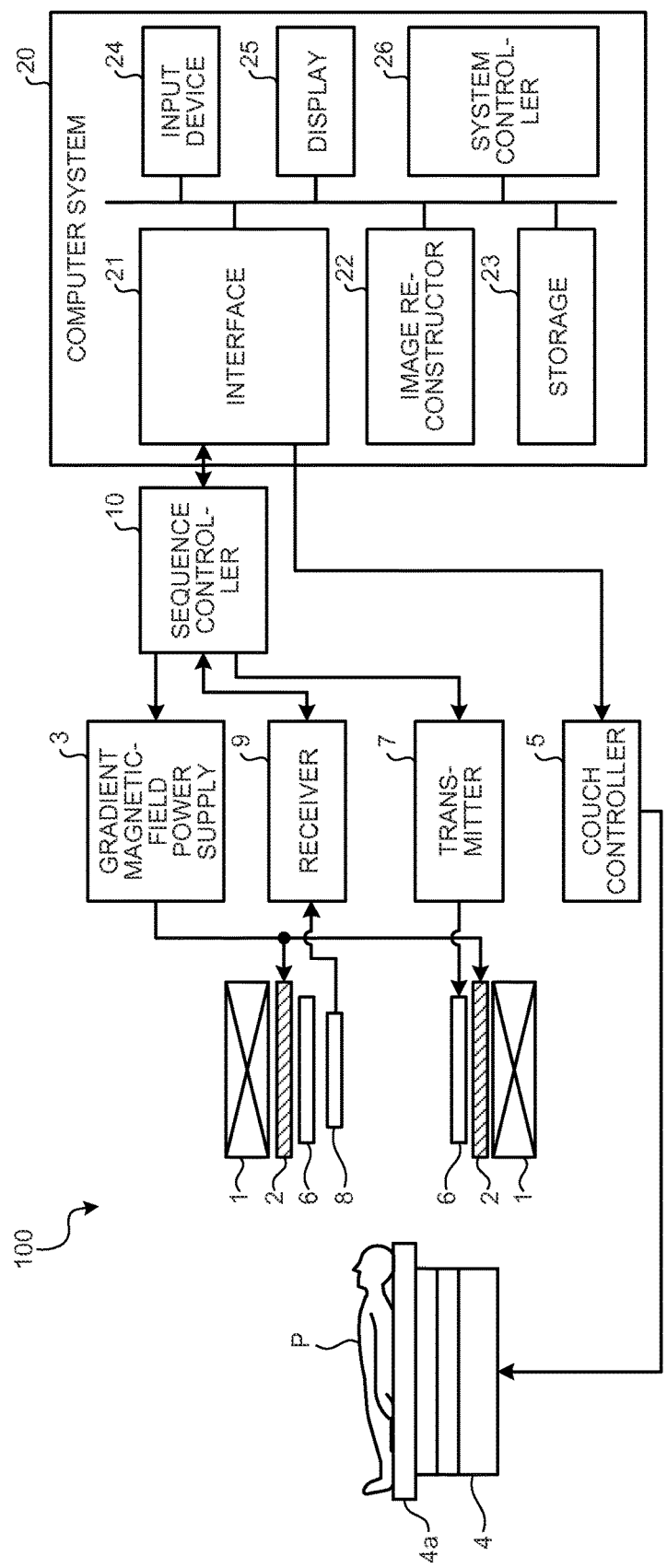
FIG. 1 shows a configuration of an MRI apparatus according to an embodiment.

FIG. 1 shows a configuration of an MRI apparatus according to an embodiment. As shown in FIG. 1, an MRI apparatus 100 includes a static magnetic field magnet 1, a gradient coil 2, a gradient magnetic-field power supply 3, a couch 4, a couch controller 5, a transmitting RF coil 6, a transmitter 7, a receiving RF coil 8, a receiver 9, a sequence controller 10, and a computer system 20.

The static magnetic field magnet 1 is a magnet formed in a hollow cylindrical shape and generates a uniform static magnetic field in a space therein. As the static magnetic field magnet 1, for example, a permanent magnet, a superconducting magnet, or the like is used.

The gradient coil 2 is formed in a hollow cylindrical shape and is arranged inside the static magnetic field magnet 1. Three coils corresponding to respective x, y, and z axes orthogonal to each other are combined to form the gradient coil 2, and these three coils generate a gradient magnetic field in which magnetic field intensity changes along the respective x, y, and z axes upon reception of current supply individually from the gradient magnetic-field power supply 3 described later. A z-axis direction is the same direction as that of the static magnetic field. The gradient magnetic-field power supply 3 supplies an electric current to the gradient coil 2.

The gradient magnetic fields along the respective x, y, and z axes generated by the gradient coil 2 respectively correspond to, for example, a slice-selecting gradient magnetic field Gss, a phase-encoding gradient magnetic field Gpe, and a read-out gradient magnetic field Gro. The slice-selecting gradient magnetic field Gss is used for determining an imaging cross section arbitrarily. The phase-encoding gradient magnetic field Gpe is used for changing a phase of a magnetic resonance signal depending on a spatial position. The read-out gradient magnetic field Gro is used for changing the frequency of the magnetic resonance signal depending on the spatial position.

The couch 4 includes a couchtop 4a on which a subject P is placed, and the couchtop 4a is inserted into a bore (an imaging space) in the gradient coil 2 in a state with the subject P being placed thereon, under control of the couch controller 5 described later. Normally, the couch 4 is installed so that a longitudinal direction is parallel to a central axis of the static magnetic field magnet 1. The couch controller 5 controls the couch 4 under control of a system controller 26, and drives the couch 4 to move the couchtop 4a in the longitudinal direction and a vertical direction.

The transmitting RF coil 6 is arranged inside the gradient coil 2 to generate an RF (Radio Frequency) pulse (a high-frequency field pulse) by a high-frequency pulse current supplied from the transmitter 7. The transmitter 7 supplies the high-frequency pulse current corresponding to a Larmor frequency to the transmitting RF coil 6. The receiving RF coil 8 is arranged inside the gradient coil 2 to receive the magnetic resonance signal emitted from the subject P due to an influence of the RF pulse. Upon reception of the magnetic resonance signal, the receiving RF coil 8 outputs the magnetic resonance signal to the receiver 9.

The receiver 9 generates magnetic resonance (MR) signal data based on the magnetic resonance signal output from the receiving RF coil 8. The receiver 9 digitally converts the magnetic resonance signal output from the receiving RF coil 8 to generate the MR signal data. In the MR signal data, pieces of information of a spatial frequency in a phase encoding direction, a read-out direction, and a slice encoding direction are associated with each other by the slice-selecting gradient magnetic field Gss, the phase-encoding gradient magnetic field Gpe, and the read-out gradient magnetic field Gro and arranged in a space k. Upon generation of the MR signal data, the receiver 9 transmits the MR signal data to the sequence controller 10.

The sequence controller 10 drives the gradient magnetic-field power supply 3, the transmitter 7, and the receiver 9 based on sequence execution data transmitted from the computer system 20 to perform scanning of the subject P. The sequence execution data is information that defines a pulse sequence indicating a procedure for performing scanning of the subject P, such as the intensity of power to be supplied to the gradient coil 2 and a timing of supplying power by the gradient magnetic-field power supply 3, the intensity of the RF signal to be transmitted to the transmitting RF coil 6 and a timing of transmitting the RF signal by the transmitter 7, and a timing of detecting the magnetic resonance signal by the receiver 9. After driving the gradient magnetic-field power supply 3, the transmitter 7, and the receiver 9 based on the sequence execution data, upon transmission of the MR signal data from the receiver 9, the sequence controller 10 transfers the MR signal data to the computer system 20.

The computer system 20 performs the overall control of the MRI apparatus 100. For example, the computer system 20 drives the respective elements included in the MRI apparatus 100 to perform scanning of the subject P and image reconstruction. The computer system 20 includes an interface 21, an image reconstructor 22, a storage 23, an input device 24, a display 25, and the system controller 26.

The interface 21 controls input and output of various signals transmitted and received between the sequence controller 10 and the interface 21. For example, the interface 21 transmits the sequence execution data to the sequence controller 10, and receives the MR signal data from the sequence controller 10. Upon reception of the MR signal data, the interface 21 stores the respective pieces of MR signal data in the storage 23 for each subject P.

The image reconstructor 22 performs post processing, that is, a reconstruction process such as Fourier transform with respect to the MR signal data stored in the storage 23, thereby generating spectral data or image data of a desired nuclear spin state in the subject P. The image reconstructor 22 stores the generated spectral data or image data in the storage 23 for each subject P.

The storage 23 stores therein various pieces of data or various programs required for processes performed by the system controller 26 described later. For example, the storage 23 stores therein the MR signal data received by the interface 21 or the spectral data or image data generated by the image reconstructor 22 for each subject P. The storage 23 is a semiconductor memory device such as a RAM (Random Access Memory), a ROM (Read Only Memory), or a flash memory, or a memory device such as a hard disk or an optical disk.

The input device 24 receives various instructions and an information input from an operator. A pointing device such as a mouse or a trackball, a selecting device such as a mode changing switch, or an input device such as a keyboard may be appropriately used as the input device 24.

The display 25 displays various pieces of information such as the spectral data or the image data under control of the system controller 26. A display device such as a liquid crystal display may be used as the display 25.

The system controller 26 includes a processor such as a CPU (Central Processing Unit) and a memory (not shown) to perform the overall control of the MRI apparatus 100. The memory stores processor-executable instructions that, when executed by the processor, cause the processor to perform the processes described later as being performed by the elements included in the system controller 26. For example, the system controller 26 generates various pieces of sequence execution data based on imaging conditions input from the operator via the input device 24, and controls scanning by transmitting the generated sequence execution data to the sequence controller 10. When the MR signal data is transmitted from the sequence controller 10 as a result of scanning, the system controller 26 controls the image reconstructor 22 to reconstruct an image based on the MR signal data.

The configuration of the MRI apparatus 100 is as explained above. With such a configuration, the MRI apparatus 100 has a function of extracting an intervertebral disk region from a plurality of positioning sagittal images, and setting an imaging region of intervertebral disks automatically based on the extracted intervertebral disk region.

Figure 2:
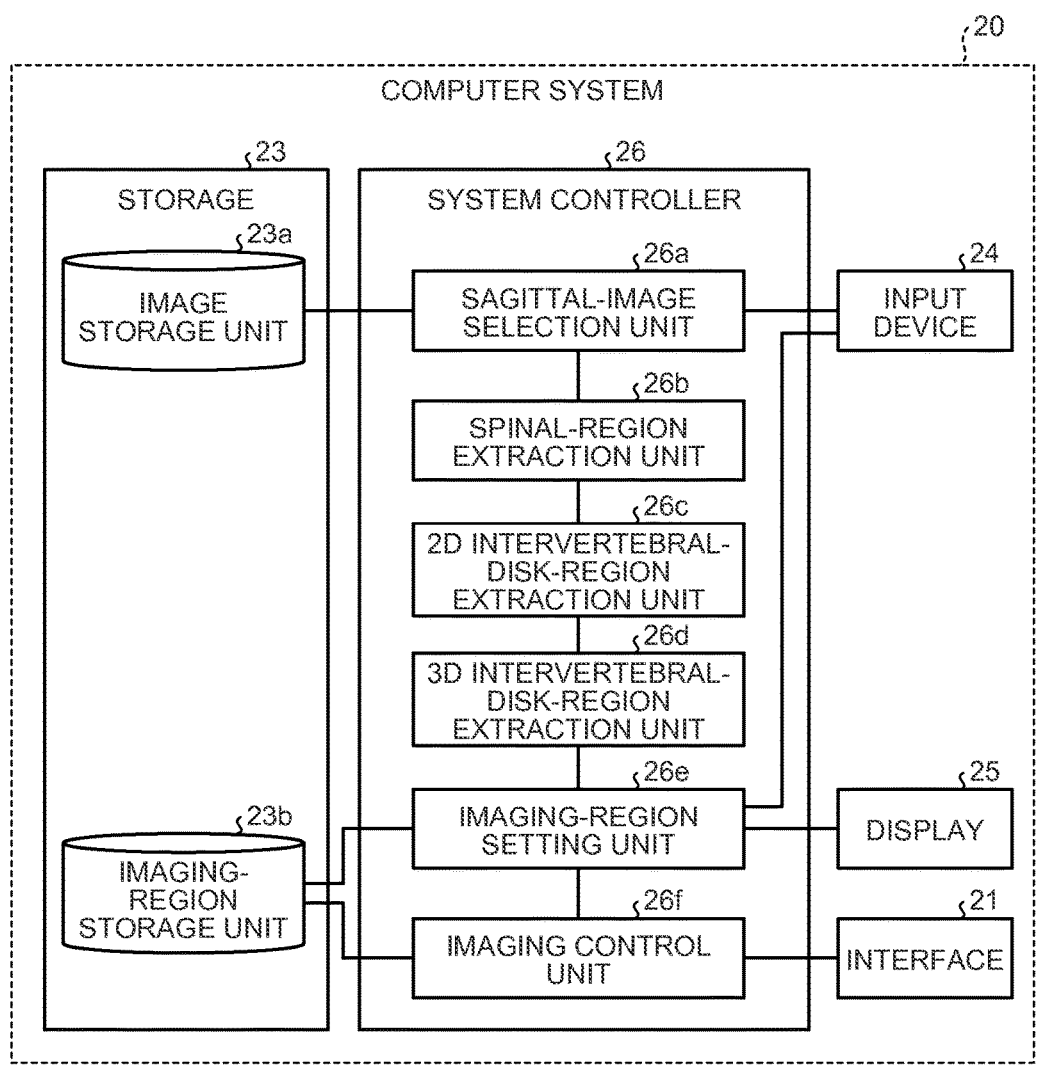
FIG. 2 is a functional block diagram of a detailed configuration of the MRI apparatus according to the embodiment.

FIG. 2 is a functional block diagram of a detailed configuration of the MRI apparatus 100 according to the present embodiment. In FIG. 2, the interface 21, the storage 23, the input device 24, and the system controller 26 are shown, of the respective elements provided in the computer system 20 shown in FIG. 1. As shown in FIG. 2, the storage 23 includes an image storage unit 23*a* and an imaging-region storage unit 23*b*. The system controller 26 includes a sagittal-image selection unit 26*a*, a spinal-region extraction unit 26*b*, a 2D intervertebral-disk-region extraction unit 26*c*, a 3D intervertebral-disk-region extraction unit 26*d*, an imaging-region setting unit 26*e*, and an imaging control unit 26*f*.

The image storage unit 23*a* stores therein image data generated by the image reconstructor 22. In the present embodiment, it is assumed that a plurality of sagittal images obtained by imaging a subject to be diagnosed are stored beforehand in the image storage unit 23*a* as the positioning sagittal images. It is assumed here that the sagittal images are respectively parallel to a sagittal cross section including intervertebral disks and a spinal canal of the subject, and include at least the intervertebral disks. It is also assumed that the positioning sagittal images are acquired according to a sequence in which the intervertebral disk having a signal value higher than a vertebral body is imaged, such as an FE (Field Echo) sequence.

For example, when it is taken into consideration that the size of the intervertebral disk in a cervical vertebra is about 2 centimeters, the size thereof in a lumbar vertebra is about 3 centimeters, the thickness of the spinal canal is about 1 centimeter, and the subject is placed by being slightly shifted from the central position of the bed, it is desired that the positioning sagittal images are acquired in such a manner that a slice thickness is about 5 to 6 millimeters, a slice gap is about 1 to 2 millimeters, and about 20 images are acquired. Under such conditions, an image may be acquired with a spatial resolution in an x-y plane of about 1 to 2 millimeters, and with an SN (Signal-to-Noise) ratio with which image processing for extracting the intervertebral disk region may be performed. However, the spatial resolution depends on TR/TE and the reception coil to be used.

The imaging-region storage unit 23b stores therein information indicating the imaging region set by the imaging-region setting unit 26e described later. In the present embodiment, the imaging region is expressed by a rectangular region referred to as "slab" including a plurality of slice regions arranged in parallel. The information indicating the imaging region includes information indicating the size of the imaging region and information indicating the position of the imaging region. For example, the information indicating the size of the imaging region includes a slice thickness, a slice gap, and the number of slices. Furthermore, for example, the information indicating the position of the imaging region includes coordinates of a central point of the slab expressing the imaging region, and an inclination of a slice surface passing through the central point. The inclination of the slice surface here is expressed by a normal vector starting from a predetermined reference point (for example, a center of the magnetic field) in apparatus coordinates and orthogonal to the slice surface passing through the center of the imaging region.

The sagittal-image selection unit 26a selects a plurality of sagittal images that visualize spines (the intervertebral disks and the vertebral bodies) from the positioning sagittal images related to the subject to be diagnosed stored in the image storage unit 23a. For example, the sagittal-image selection unit 26a reads out the positioning sagittal images related to the subject to be diagnosed from the image storage unit 23a, and creates an average image of the read positioning sagittal images. The sagittal-image selection unit 26a creates a difference image between the created average image and each positioning sagittal image. The difference image including the spines, of the created difference images, has a lower signal value in the spinal region than the difference image not including the spines.

Figure 3:
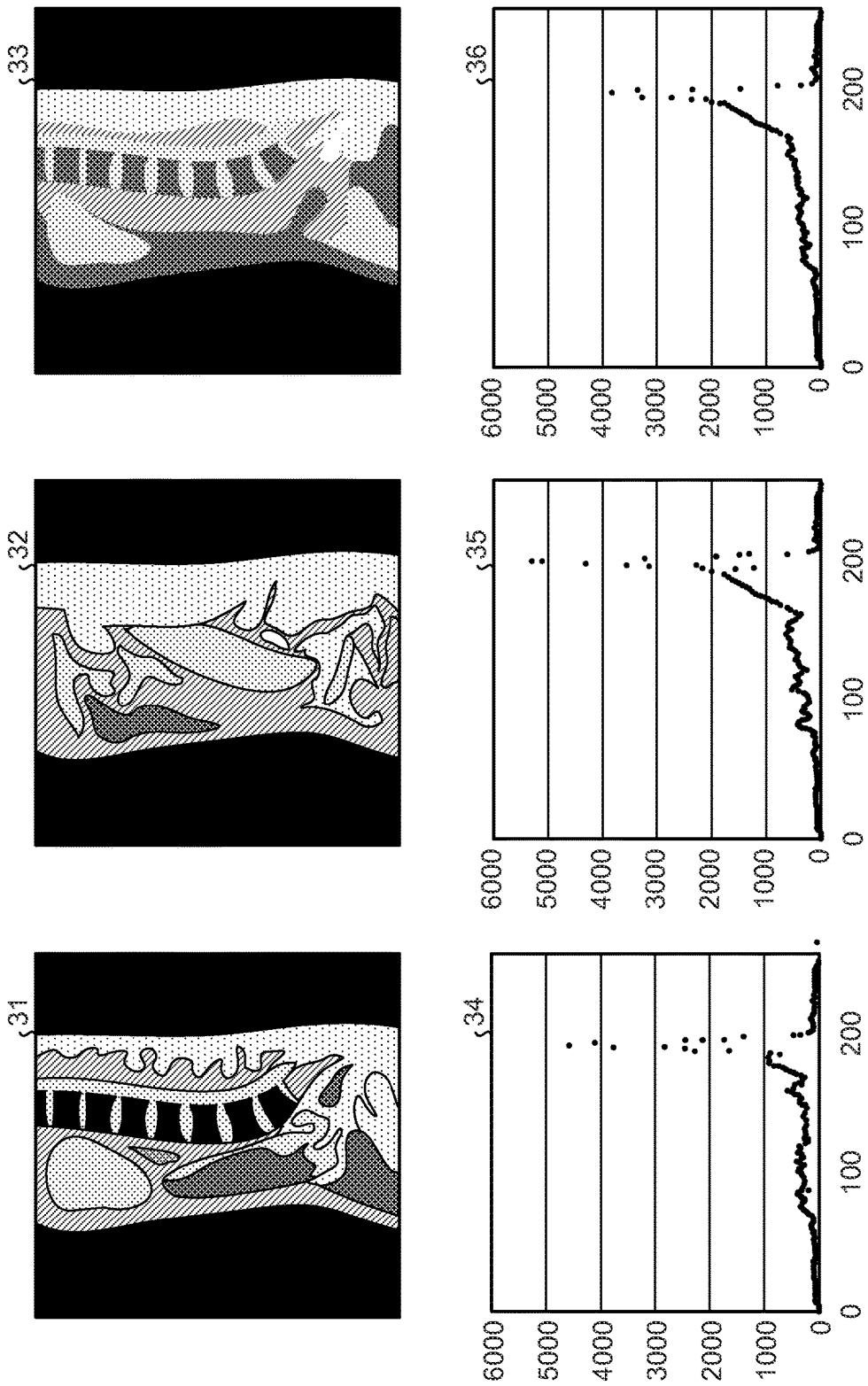
FIG. 3 is an example of a positioning sagittal image to be processed by a sagittal-image selection unit according to the embodiment.

FIG. 3 is an example of a positioning sagittal image to be processed by the sagittal-image selection unit 26a according to the present embodiment. In FIG. 3, an image 31 is the positioning sagittal image including the spines, an image 32 is the positioning sagittal image not including the spines, and an image 33 is the average image created based on a plurality of positioning sagittal images. A graph 34 indicates distribution of signal values in the image 31, a graph 35 indicates distribution of signal values in the image 32, and a graph 36 indicates distribution of signal values in the image 33. In the graphs 34 to 36, a horizontal axis indicates a position (0 to 256) in an x-axis direction (a horizontal direction in FIG. 3) of each pixel included in the images, and a vertical axis indicates a total of the signal values of pixels at the respective positions. As shown in FIG. 3, for example, the positioning sagittal image including the spines (the image 31) has lower signal values by 30% to 50% in the spinal region (a range of about 120 to 150 shown in the graphs 34 and 35) as compared to the positioning sagittal image not including the spines (the image 32).

Figure 4:
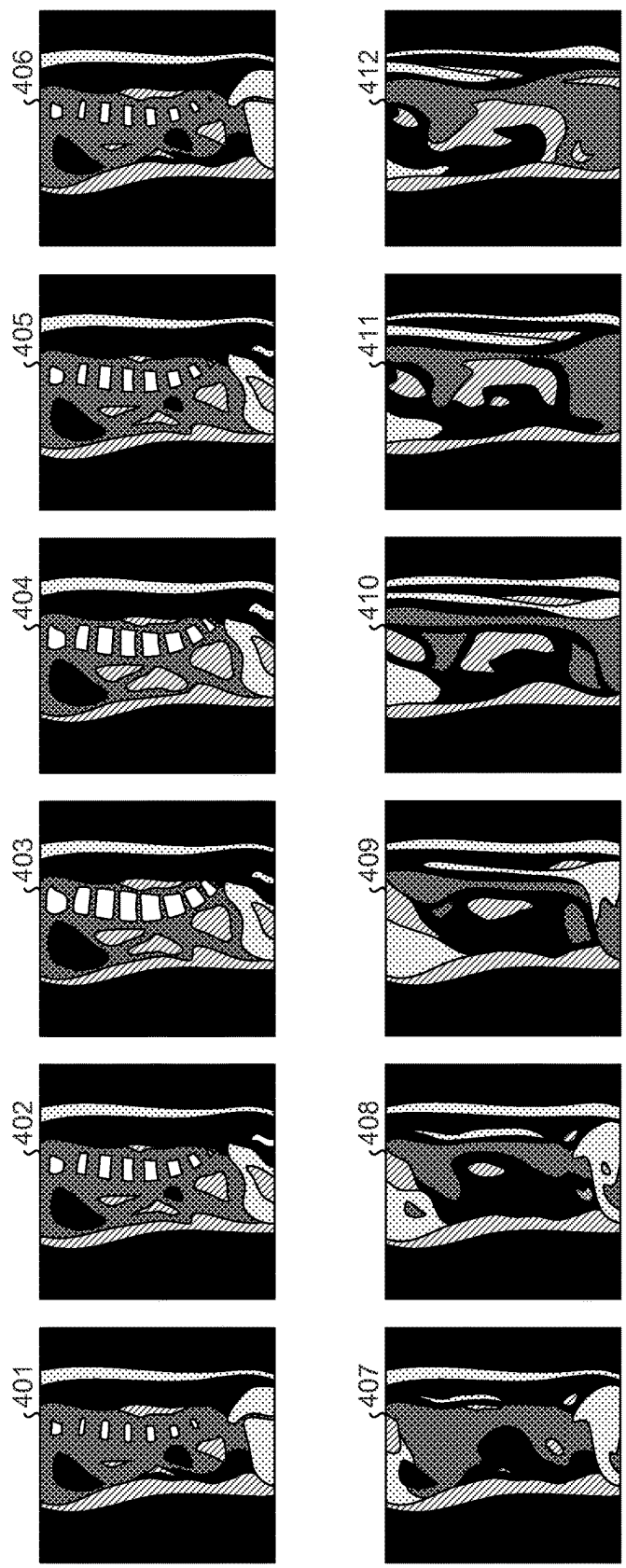
FIG. 4 is an example of a difference image created by a sagittal-image selection unit according to the embodiment.

FIG. 4 is an example of a difference image created by the sagittal-image selection unit 26a according to the present embodiment. In FIG. 4, images 401 to 406 are difference images of the sagittal images respectively including the spines, and images 407 to 412 are difference images of the sagittal images respectively not including the spines. Normally, because the images that visualize the spinal region are only a part of the positioning sagittal images obtained by imaging the subject to be diagnosed, when an average image is created, the signal values of the spinal region in the average image become relatively high. Accordingly, when the average image is subtracted from the positioning sagittal image to create a difference image, as shown in FIG. 4, there is a significant difference in the signal values of the spinal region in the sagittal images including the spinal region (the images 401 to 406) and the sagittal images not including the spinal region (the images 407 to 412). In the example shown in FIG. 4, as a result of subtraction of the average image from the positioning sagittal image, the signal value is replaced by 0 in a pixel having a signal value equal to or larger than 0, and then signs of the signal values are inverted for all the pixels.

The sagittal-image selection unit 26a also removes a fat region from the created difference images. For example, the sagittal-image selection unit 26a searches for a peak of a profile in the x-axis direction in the average image of the positioning sagittal images, and obtains a signal value at a point where an inclination of a curved line of the profile becomes a predetermined value or below by descending from the peak in a positive direction and a negative direction of the x axis. The sagittal-image selection unit 26a determines a threshold based on a larger signal value of the obtained two signal values, and performs threshold processing to each difference image of the positioning sagittal images, thereby removing the fat region from the respective difference images.

Subsequently, the sagittal-image selection unit 26a selects an image that visualizes the spines (intervertebral disks and vertebral bodies) from a plurality of difference images. For example, the sagittal-image selection unit 26a detects the highest signal value of the signal values of the pixels included in the respective difference images, and counts the number of pixels having a value of 80% or more of the detected signal value in the respective difference images. The sagittal-image selection unit 26a selects five difference images in descending order of the counted number of pixels as the difference images that visualize the spines. For example, in the example shown in FIG. 4, the sagittal-image selection unit 26a selects five images 402 to 406.

In the present embodiment, an example in which the sagittal-image selection unit 26a creates an average image of the positioning sagittal images related to the subject to be diagnosed is explained. However, the present embodiment is not limited thereto. For example, the sagittal-image selection unit 26a may create an MIP (Maximum Intensity Projection) image instead of creating the average image. In this case, it is desired to remove the fat region from the respective positioning sagittal images before creating the MIP image.

The spinal-region extraction unit 26b extracts the spinal regions from each of the sagittal images parallel to the sagittal cross section including intervertebral disks and a spinal canal of the subject and including at least the intervertebral disks. For example, the spinal-region extraction unit 26b creates an average image of the difference images selected by the sagittal-image selection unit 26a. In the selected difference images, while a vertebral region has high signal values in almost all difference images, there is a variation in the signal values in the respective difference images of organs seen in the abdominal region. Therefore, the vertebral region may be emphasized by creating the average image of the difference images. Thereafter, the spinal-region extraction unit 26b creates a binarized vertebral body image by binarizing the created average image.

Figure 5:
FIG. 5 is an example of a binarized vertebral body image created by a spinal-region extraction unit according to the embodiment.

FIG. 5 is an example of a binarized vertebral body image created by the spinal-region extraction unit 26b according to the present embodiment. As described above, the average image of the difference images is created to emphasize the vertebral region, and by binarizing the average image, as shown in FIG. 5, the binarized vertebral body image in which the vertebral region is clearly visualized may be created.

Subsequently, the spinal-region extraction unit 26b extracts the spinal region from the created binarized vertebral body image. For example, the spinal-region extraction unit 26b performs Morphology processing with respect to the binarized vertebral body image to extract a region indicating the spinal region. The spinal-region extraction unit 26b designates the extracted region as a mask indicating the spinal region.

Figure 6:
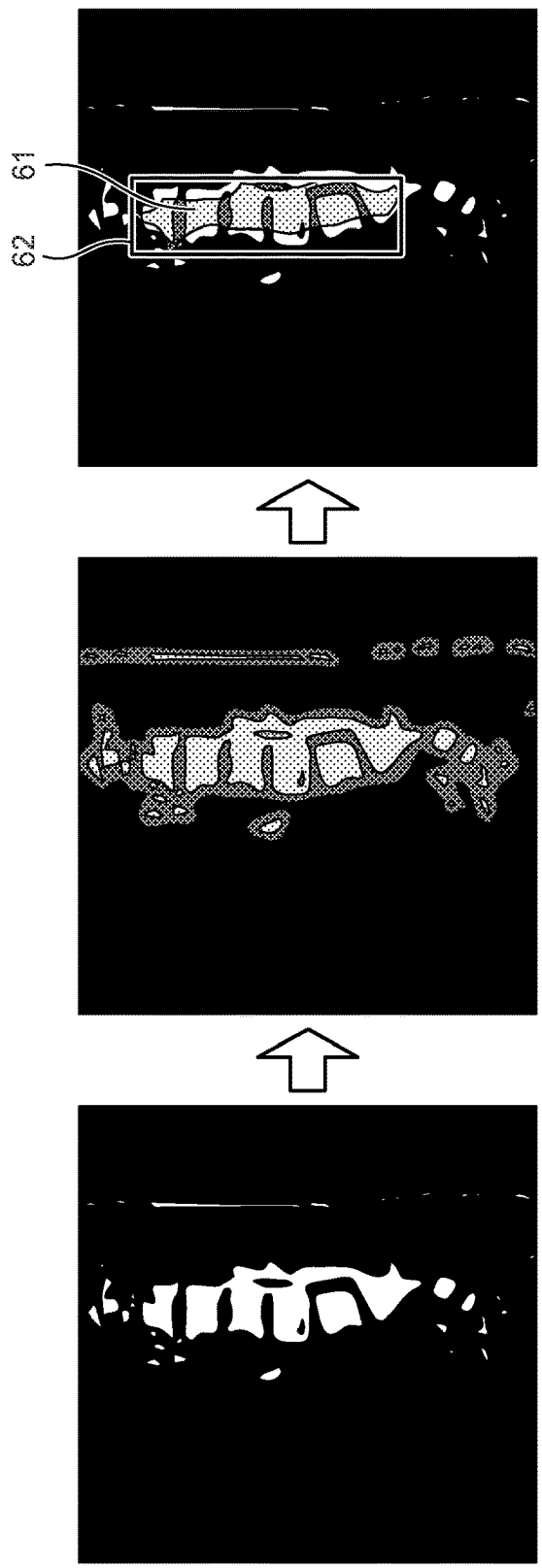
FIG. 6 is an explanatory diagram of an example of extraction of a spinal region performed by the spinal-region extraction unit according to the embodiment.

FIG. 6 is an explanatory diagram of an example of extraction of a spinal region performed by the spinal-region extraction unit 26b according to the present embodiment. An image shown on the left side in FIG. 6 is an example of the binarized vertebral body image created by the spinal-region extraction unit 26b. For example, as shown in the center of FIG. 6, the spinal-region extraction unit 26b performs Dilation processing with respect to the binarized vertebral body image. Thereafter, as shown on the right side in FIG. 6, the spinal-region extraction unit 26b performs Erosion processing with respect to the binarized vertebral body image to which the Dilation processing has been performed. At this time, the spinal-region extraction unit 26b determines the number of pixels to be processed by the Dilation processing or the Erosion processing based on the number of pixels of the positioning sagittal images and an FOV (Field Of View). As a result of performing the Dilation processing and the Erosion processing, when the number of regions finally obtained in the binarized vertebral body image is not one, the spinal-region extraction unit 26b leaves only the largest region, and removes the other small regions from the binarized vertebral body image. As shown on the right side in FIG. 6, the spinal-region extraction unit 26b creates a rectangular region 62 surrounded by the largest value and the smallest value in the x-axis direction and the y-axis direction, respectively, of a region 61 finally obtained, and designates the region as a mask indicating the spinal region.

The 2D intervertebral-disk-region extraction unit 26c extracts a two-dimensional intervertebral disk region respectively from the plurality of spinal regions extracted from the plurality of sagittal images. For example, the 2D intervertebral-disk-region extraction unit 26c applies the mask of the spinal region created by the spinal-region extraction unit 26b to the respective difference images selected by the sagittal-image selection unit 26a, and performs an edge enhancement process with respect to the pixels in a mask region in the y-axis direction. At this time, after the image in the mask region is binarized, the 2D intervertebral-disk-region extraction unit 26c may perform the Dilation processing and the Erosion processing sequentially with respect to the binarized image.

Figure 7:
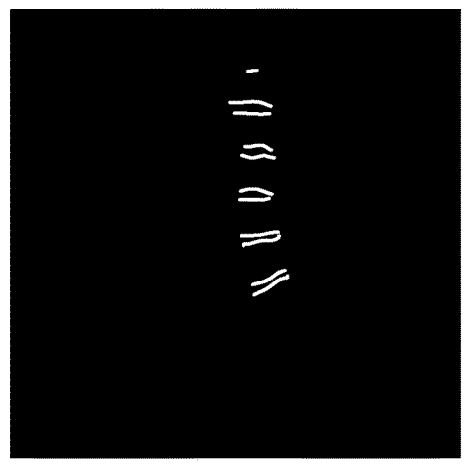
FIG. 7 is an example of a result of an edge enhancement process performed by a 2D intervertebral-disk-region extraction unit according to the embodiment.

FIG. 7 is an example of a result of an edge enhancement process performed by the 2D intervertebral-disk-region extraction unit 26c according to the present embodiment. As shown in FIG. 7, a plurality of lines roughly along the x-axis direction are visualized on the respective difference images by the edge enhancement process. The 2D intervertebral-disk-region extraction unit 26c obtains a midpoint of the lines visualized by the edge enhancement process and obtains a two-dimensional spline curve respectively passing through respective midpoints for each of the difference images. Thereafter, the 2D intervertebral-disk-region extraction unit 26c obtains a profile of signal values along the obtained spline curve. The 2D intervertebral-disk-region extraction unit 26c calculates an average value of a plurality of high signal regions in which the signal value becomes equal to or larger than a predetermined value in the obtained profile, and designates each of the calculated average values as a signal value of the intervertebral disk region, respectively.

Subsequently, the 2D intervertebral-disk-region extraction unit 26c performs Region Growing processing by designating a region detected as the high signal region (in practice, a pixel positioned in a section on the spline curve) as a seed point for the respective difference images. At this time, the 2D intervertebral-disk-region extraction unit 26c uses a value calculated based on the signal value of the intervertebral disk region obtained by the above processing as a threshold, as a terminating condition of the Region Growing processing. After performing the Region Growing processing, the 2D intervertebral-disk-region extraction unit 26c may perform two-pixel Erosion processing and one-pixel Dilation processing sequentially.

Thereafter, the 2D intervertebral-disk-region extraction unit 26c obtains a least square line for each of the intervertebral disk regions visualized in the respective difference images. The 2D intervertebral-disk-region extraction unit 26c then obtains a normal line to the least square line for the intervertebral disk region located at the uppermost and lowermost positions in the respective difference images, and performs the edge enhancement process in a direction along the normal line. When an edge is detected at two points within a predetermined distance in the respective difference images by the edge enhancement process, the 2D intervertebral-disk-region extraction unit 26c performs the Region Growing processing by designating the midpoint between the two points as a seed point. Also at this time, the 2D intervertebral-disk-region extraction unit 26c uses a value calculated based on the signal value of the intervertebral disk region obtained by the above processing as a threshold, as the terminating condition of the Region Growing processing.

The 3D intervertebral-disk-region extraction unit 26d extracts a three-dimensional intervertebral disk region spanning across the sagittal images based on the two-dimensional intervertebral disk regions extracted respectively from each of the spinal regions by the 2D intervertebral-disk-region extraction unit 26c. For example, the 3D intervertebral-disk-region extraction unit 26d performs the Region Growing processing with respect to all the positioning sagittal images related to the subject to be diagnosed, designating the two-dimensional intervertebral disk regions extracted by the 2D intervertebral-disk-region extraction unit 26c as seed regions. At this time, the 3D intervertebral-disk-region extraction unit 26d uses a value calculated from the size (the number of pixels) of the two-dimensional intervertebral disk region extracted by the 2D intervertebral-disk-region extraction unit 26c as the terminating condition of the Region Growing processing.

The imaging-region setting unit 26e sets imaging regions of a positioning coronal image, a diagnostic sagittal image, and a diagnostic intervertebral disk image based on the three-dimensional intervertebral disk region extracted by the 3D intervertebral-disk-region extraction unit 26d. The imaging-region setting unit 26e stores information indicating respective set imaging regions in the imaging-region storage unit 23b. For example, the imaging-region setting unit 26e sets the imaging region of the coronal image including the intervertebral disks based on the three-dimensional intervertebral disk regions extracted by the 3D intervertebral-disk-region extraction unit 26d. Specifically, the imaging-region setting unit 26e calculates coordinates of a barycentric point for each of the three-dimensional intervertebral disk regions extracted by the 3D intervertebral-disk-region extraction unit 26d. Furthermore, the imaging-region setting unit 26e calculates mean values of an x-coordinate, a y-coordinate, and a z-coordinate of the calculated respective barycentric points, thereby obtaining three-dimensional average coordinates of the respective barycentric points.

The imaging-region setting unit 26e sets the calculated average coordinates as a central point of the imaging region of the positioning coronal image. In the present embodiment, the imaging-region setting unit 26e sets the inclination of the imaging region of the positioning coronal image so that the imaging region is parallel to a head and feet direction (a moving direction of the couchtop 4a). Further, the imaging-region setting unit 26e sets values set by an operator beforehand as imaging conditions for the slice thickness, the slice gap, and the number of slices that determine the size of the imaging region of the positioning coronal image. The imaging-region setting unit 26e may automatically determine the slice thickness, the slice gap, and the number of slices of the imaging region of the positioning coronal image so as to be a size including all the barycentric points of the respective intervertebral disk regions.

For example, the imaging-region setting unit 26e sets the imaging region of the diagnostic sagittal image based on the three-dimensional intervertebral disk regions extracted by the 3D intervertebral-disk-region extraction unit 26d. Specifically, the imaging-region setting unit 26e calculates coordinates of the barycentric point for each of the three-dimensional intervertebral disk regions extracted by the 3D intervertebral-disk-region extraction unit 26d. Furthermore, the imaging-region setting unit 26e calculates mean values of the x-coordinate, the y-coordinate, and the z-coordinate of the calculated respective barycentric points, thereby obtaining three-dimensional average coordinates of the respective barycentric points.

The imaging-region setting unit 26e sets the calculated average coordinates as a central point of the imaging region of the diagnostic sagittal image. The imaging-region setting unit 26e projects the coordinates of the barycentric points of the respective intervertebral disk regions to a coronal cross section passing through the calculated average coordinates, to calculate the least square line for each of the respective projected barycentric points. The imaging-region setting unit 26e sets the inclination of the calculated least square line as the inclination of the imaging region of the diagnostic sagittal image. Furthermore, the imaging-region setting unit 26e sets values set by an operator beforehand as imaging conditions for the slice thickness, the slice gap, and the number of slices that determine the size of the imaging region of the diagnostic sagittal image.

For example, the imaging-region setting unit 26e sets the imaging region of the diagnostic intervertebral disk image based on the three-dimensional intervertebral disk regions extracted by the 3D intervertebral-disk-region extraction unit 26d. Specifically, the imaging-region setting unit 26e obtains a least square surface for each of the three-dimensional intervertebral disk regions extracted by the 3D intervertebral-disk-region extraction unit 26d. The imaging-region setting unit 26e sets the inclination of the obtained least square surface as the inclination of the imaging region of the respective diagnostic intervertebral disk images. The imaging-region setting unit 26e sets the coordinates of each barycentric point of the respective three-dimensional intervertebral disk regions as a central point of the imaging region of the respective diagnostic intervertebral disk images.

Subsequently, the imaging-region setting unit 26e receives an operation to select an imaging region to be imaged from the set imaging regions of the diagnostic intervertebral disk images from an operator. For example, the imaging-region setting unit 26e displays the set imaging regions of the diagnostic intervertebral disk images on the display 25, and displays a GUI (Graphical User Interface) for selecting the imaging region to be imaged from the displayed imaging regions on the display 25.

Figure 8:
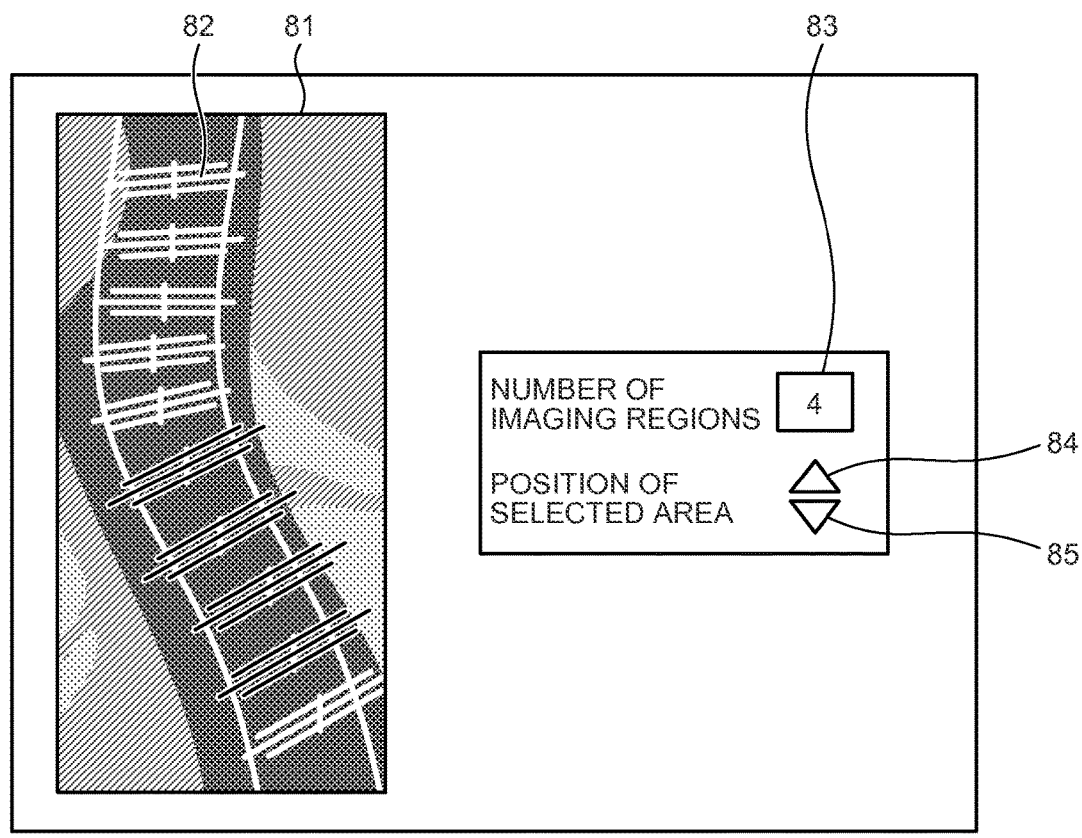
FIG. 8 is an example of a GUI displayed by an imaging-region setting unit according to the embodiment.

FIG. 8 is an example of a GUI displayed by the imaging-region setting unit 26e according to the present embodiment. As shown in FIG. 8, for example, the imaging-region setting unit 26e displays a positioning sagittal image 81, and arranges and displays a graphic 82 expressing the set imaging regions of the diagnostic intervertebral disk images thereon. At this time, the imaging-region setting unit 26e displays the positioning sagittal image that visualizes the largest spinal region, of the positioning sagittal images related to the subject to be diagnosed. For example, when the sagittal-image selection unit 26a counts the number of pixels having a value of 80% or more of the highest signal value, the imaging-region setting unit 26e displays the positioning sagittal image corresponding to the difference image having the largest number of counted pixels.

Furthermore, as shown in FIG. 8, for example, the imaging-region setting unit 26e displays a text box 83 to input the number of imaging regions to be selected as imaging objects. Upon input of the number of the imaging regions in the text box 83, the imaging-region setting unit 26e selects the imaging regions to the input number from the displayed imaging regions. At this time, for example, the imaging-region setting unit 26e selects the imaging regions sequentially from the top by the number input in the text box 83 from the displayed imaging regions. Alternatively, the imaging-region setting unit 26e may select the imaging regions sequentially from the bottom, or may select the imaging regions from the imaging regions near the center in the vertical direction.

Further, as shown in FIG. 8, for example, the imaging-region setting unit 26e displays an upward navigation button 84 and a downward navigation button 85 for selecting the imaging regions to be imaged. When the upward navigation button 84 is pressed, the imaging-region setting unit 26e sets the imaging region at the lowermost position of the imaging regions selected at that point in time to a non-selected state, and sets the imaging region one above the imaging region at the uppermost position to a selected state. The imaging-region setting unit 26e repeats the process every time the upward navigation button 84 is pressed. On the other hand, when the downward navigation button 85 is pressed, the imaging-region setting unit 26e sets the imaging region at the uppermost position of the imaging regions selected at that point in time to the non-selected state, and sets the imaging region one below the imaging region at the lowermost position to the selected state. The imaging-region setting unit 26e repeats the process every time the downward navigation button 85 is pressed.

As described above, the imaging-region setting unit 26e changes the imaging regions selected as the imaging objects based on the number of the imaging regions input in the text box 83 and the operation of pressing the upward navigation button 84 or the downward navigation button 85. For example, the imaging-region setting unit 26e performs control so that the selected imaging regions are displayed in a different color from other imaging regions. For example, in the example shown in FIG. 8, such a state is shown that the number of imaging regions selected as the imaging objects is "4", and the 6th to 9th imaging regions from above are selected as the imaging objects. When the imaging regions are selected by an operator, the imaging-region setting unit 26e transmits information that identifies the selected imaging regions to the imaging control unit 26f described later.

The imaging control unit 26f acquires various slice images based on the imaging conditions set by the operator and the imaging regions set by the imaging-region setting unit 26e. For example, the imaging control unit 26f acquires slice images of the imaging regions selected as the imaging objects, of the imaging regions of the diagnostic intervertebral disk images set by the imaging-region setting unit 26e.

Specifically, when the information that identifies the selected imaging regions is transmitted from the imaging-region setting unit 26e, the imaging control unit 26f reads the information indicating the imaging regions from the imaging-region storage unit 23b. The imaging control unit 26f generates sequence execution data for taking the slice images of the selected imaging regions based on the read information, and transmits the generated sequence execution data to the sequence controller 10. Accordingly, the sequence controller 10 drives the gradient magnetic-field power supply 3, the transmitter 7, and the receiver 9 to acquire the slice images of the selected imaging regions.

A process procedure for setting imaging regions and imaging intervertebral disks performed by the MRI apparatus 100 according to the present embodiment is explained next.

FIG. 9 is a flowchart of a process procedure for setting imaging regions performed by the MRI apparatus 100 according to the present embodiment. As shown in FIG. 9, for example, upon reception of an instruction to start imaging from an operator via the input device 24 (YES at Step S101), the MRI apparatus 100 performs the following process.

First, the imaging control unit 26f acquires a plurality of positioning sagittal images of the subject to be diagnosed (Step S102). The respective positioning sagittal images acquired here are stored in the storage 23.

Thereafter, the sagittal-image selection unit 26a selects a sagittal image including the spines (the intervertebral disks and the vertebral bodies) from the positioning sagittal images of the subject to be diagnosed stored in the image storage unit 23a (Step S103). The sagittal-image selection unit 26a selects a plurality of difference images that visualize the spines from the difference images between the respective positioning sagittal images and the average image.

Subsequently, the spinal-region extraction unit 26b extracts the spinal region from the respective sagittal images (difference images) selected by the sagittal-image selection unit 26a (Step S104). Thereafter, the 2D intervertebral-disk-region extraction unit 26c extracts the two-dimensional intervertebral disk region from the respective spinal regions extracted by the spinal-region extraction unit 26b (Step S105).

The 3D intervertebral-disk-region extraction unit 26d then extracts the three-dimensional intervertebral disk region spanning across the positioning sagittal images based on the two-dimensional intervertebral disk regions extracted respectively from the spinal regions by the 2D intervertebral-disk-region extraction unit 26c (Step S106).

Subsequently, the imaging-region setting unit 26e sets the imaging regions of the positioning coronal image, the diagnostic sagittal image, and the diagnostic intervertebral disk image based on the three-dimensional intervertebral disk region extracted by the 3D intervertebral-disk-region extraction unit 26d (Steps S107 to S109).

Thereafter, the imaging-region setting unit 26e displays the set imaging regions of the diagnostic intervertebral disk image on the display 25 (Step S110). The imaging-region setting unit 26e also displays the GUI for selecting the imaging regions to be imaged from the displayed imaging regions on the display 25.

Upon selection of the imaging regions to be imaged by the operator (YES at Step S111), the imaging control unit 26f acquires the slice images of the selected imaging regions as the diagnostic intervertebral disk image (Step S112).

As described above, the MRI apparatus 100 according to the present embodiment extracts the intervertebral disk region from the plurality of positioning sagittal images, and automatically sets the imaging regions of the intervertebral disks based on the extracted intervertebral disk region. Accordingly, according to the present embodiment, the imaging regions of the intervertebral disks may be easily set in the diagnostic imaging examination in which imaging of the intervertebral disks is performed.

Conventionally, in the diagnostic imaging examination of intervertebral disk injury using the MRI apparatus, slice images parallel to the intervertebral disks and including the intervertebral disks are acquired in order to evaluate the intervertebral disk injury of a patient. In the diagnostic imaging examination, because it is unknown which of the intervertebral disks is ruptured, a plurality of intervertebral disks are normally imaged. Therefore, an operator acquires a positioning image (also "locator image") for confirming the position of the intervertebral disk, and sets an imaging region (also "imaging ROI (Region Of Interest)") including respective intervertebral disks on the image. If a subject moves in the procedure performed by the operator, the position of the imaging region set on the positioning image and the actual position of the intervertebral disk deviates from each other. Therefore, the intended cross section may not be imaged, and accurate diagnosis may not be performed. Furthermore, because the operator manually sets the imaging region, a time required for one examination becomes long, and as a result, the number of examinations that may be performed in one day decreases.

On the other hand, in the present embodiment, because the imaging regions of the intervertebral disks are automatically set based on a plurality of positioning sagittal images, the time required for setting the imaging regions of the intervertebral disks may be reduced. Accordingly, the imaging regions may be set while the subject remains immobile, and the intended cross sections may be imaged. Further, because the time required for one examination may be reduced, and as a result, the number of examinations that may be performed in one day may be increased.

The MRI apparatus 100 explained in the above embodiment may be modified in various forms without changing the basic configurations shown in FIGS. 1 and 2. Several modifications of the embodiment are explained below.

First, in the above embodiment, an example in which the imaging regions of the positioning coronal image, the diagnostic sagittal image, and the diagnostic intervertebral disk image are continuously set based on the plurality of positioning sagittal images has been explained. Meanwhile, for example, after the imaging-region setting unit 26e sets the imaging region of the positioning coronal image, the set imaging region may be arranged and displayed on the positioning sagittal image, thereby prompting an operator to make confirmation. In this case, the imaging-region setting unit 26e receives an operation to change the position and the size of the imaging region in the displayed positioning coronal image from the operator, and updates the information of the imaging region stored in the imaging-region storage unit 23b according to the received operation. When the imaging region of the diagnostic sagittal image and the imaging region of the diagnostic intervertebral disk image have been already set, the imaging-region setting unit 26e changes a central point for the imaging regions of the diagnostic sagittal image and the diagnostic intervertebral disk image based on the central point of the imaging region of the changed positioning coronal image.

In the above embodiment, an example in which after the imaging regions of the positioning coronal image, the diagnostic sagittal image, and the diagnostic intervertebral disk image have been set by the imaging-region setting unit 26e, the imaging control unit 26f acquires only the diagnostic intervertebral disk image has been explained. Meanwhile, for example, the imaging control unit 26f may further acquire both or one of the positioning coronal image and the diagnostic sagittal image.

For example, when the imaging control unit 26f is to acquire the positioning coronal images, the imaging-region setting unit 26e may prompt an operator to make confirmation by arranging and displaying the imaging regions of the diagnostic sagittal image on the acquired positioning coronal image. In this case, the imaging-region setting unit 26e receives an operation to change the position and the size of the imaging regions in the displayed diagnostic sagittal image from the operator, and updates the information of the imaging region stored in the imaging-region storage unit 23b according to the received operation. In this case, the imaging-region setting unit 26e changes the central point for the already set imaging region of the diagnostic intervertebral disk image based on the central point of the changed imaging region.

In the above embodiment, an example in which the imaging-region setting unit 26e displays the imaging regions of the diagnostic intervertebral disk image on the positioning sagittal image has been explained. Meanwhile, for example, when the imaging control unit 26f is to acquire the diagnostic sagittal images, the imaging-region setting unit 26e may prompt an operator to make confirmation by arranging and displaying the imaging regions of the diagnostic intervertebral disk image on the acquired diagnostic sagittal image. In this case, similarly to the above embodiment, the imaging-region setting unit 26e displays on the display 25 the GUI for selecting the imaging regions to be imaged, from the displayed imaging regions of the diagnostic intervertebral disk image. In this case, the imaging-region setting unit 26e receives an operation to change the position and the size of the displayed imaging regions from the operator, and updates the information of the imaging regions stored in the imaging-region storage unit 23b according to the received operation.

In the above embodiment, an example in which after the spinal region is extracted from the plurality of positioning sagittal images, the intervertebral disk region is extracted by applying image processing such as the Region Growing processing with respect to the extracted spinal region has been explained. Meanwhile, when the imaging control unit 26f is to acquire the positioning coronal images, the intervertebral disk region may be re-extracted by using the acquired positioning coronal images. In this case, after the imaging-region setting unit 26e sets the imaging regions of the positioning coronal images, the imaging control unit 26f acquires the positioning coronal images based on the set imaging regions. The imaging-region setting unit 26e then applies image processing such as the Region Growing processing with respect to the acquired positioning coronal images similarly to the processing applied to the positioning sagittal image, thereby re-extracting the intervertebral disk region. Thus, by using the plurality of positioning sagittal images and positioning coronal images, the intervertebral disk region may be extracted based on the position information in two directions orthogonal to each other. Accordingly, the imaging regions of the diagnostic intervertebral disk image may be set highly accurately.

In the above embodiment, an example in which the system controller 26 includes the spinal-region extraction unit 26b, the 2D intervertebral-disk-region extraction unit 26c, and the 3D intervertebral-disk-region extraction unit 26d has been explained. However, the functions of these extraction units may be put together and incorporated in one extraction unit. That is, the extraction unit extracts the intervertebral disk region spanning across the plurality of sagittal images from the spines visualized in the sagittal images based on the sagittal images including at least the intervertebral disks of the subject. The method of extracting the intervertebral disk region by the extraction unit is not limited to the method performed by the spinal-region extraction unit 26b, the 2D intervertebral-disk-region extraction unit 26c, and the 3D intervertebral-disk-region extraction unit 26d.

For example, the extraction unit extracts the two-dimensional intervertebral disk region respectively from the spines visualized in each of the sagittal images, and extracts the three-dimensional intervertebral disk region spanning across the sagittal images based on the extracted two-dimensional intervertebral disk regions. In this case, for example, the storage 23 stores therein a pattern indicating a standard shape of spines and positions of the intervertebral disk regions in the spines. The extraction unit reads the pattern stored in the storage 23 and performs pattern matching for collating the read pattern with the positioning sagittal image for each of the positioning sagittal images, thereby extracting the two-dimensional intervertebral disk regions from the spines visualized in the positioning sagittal images.

For example, the extraction unit may extract the three-dimensional intervertebral disk region directly from the plurality of sagittal images. In this case, for example, the storage 23 stores therein a standard three-dimensional shape of the spines and a three-dimensional pattern indicating the positions of the three-dimensional intervertebral disk regions in the spines. The extraction unit then reads the three-dimensional pattern stored in the storage 23, and performs pattern matching for collating the read three-dimensional pattern with volume data or multi-slice data including the plurality of positioning sagittal images, thereby extracting the three-dimensional intervertebral disk regions from the positioning sagittal images.

In the above embodiment, an example in which an image acquired according to the sequence in which the intervertebral disk having a signal value higher than the vertebral body is imaged is used as the positioning sagittal image has been explained. However, the sequence for imaging the positioning sagittal image is not limited thereto.

For example, as the sagittal images, images acquired according to a sequence in which protons of water and fat are imaged with a phase thereof being shifted from each other may be used. In the image in which phases of protons of water and fat are shifted from each other, which is acquired according to such a sequence, is also referred to as "out of phase image". Normally, because the ratio of water and fat contained in the intervertebral disks and the vertebral bodies is different from each other, in the out of phase image, a boundary between the intervertebral disks and the vertebral bodies is clearly visualized. Therefore, by using the out of phase image as the positioning sagittal image, accuracy of extracting the intervertebral disk regions may be improved.

In the above embodiment, an example in which the intervertebral disk regions extracted based on the plurality of sagittal images are directly used to set the imaging regions of the intervertebral disk image has been explained. However, the extracted intervertebral disk regions may be corrected according to need. In this case, for example, the extraction unit corrects extraction results of the intervertebral disk regions based on the position relation of the plurality of intervertebral disk regions extracted from the sagittal images.

For example, the extraction unit determines whether there is an intervertebral disk region having been failed to be extracted based on the position relation of the extracted intervertebral disk regions, and when there is an intervertebral disk region having been failed to be extracted, the extraction unit adds the intervertebral disk region. Specifically, as explained in the processing performed by the 2D intervertebral-disk-region extraction unit $26c$ in the above embodiment, the extraction unit obtains the two-dimensional spline curve passing through the midpoint of the plurality of lines visualized by the edge enhancement process for each of the difference images in which the spines are visualized, to detect the intervertebral disk region based on the profile of the signal values along the spline curve. Thereafter, the extraction unit obtains a distance between the intervertebral disk regions along the spline curve, for each set of adjacent intervertebral disk regions, for each of the intervertebral disk regions detected on the spline curve. Subsequently, the extraction unit determines whether there is a set of intervertebral disk regions having a considerably larger distance between the intervertebral disk regions as compared to other sets. When there is the set of intervertebral disk regions having a considerably large distance between the intervertebral disk regions, the extraction unit adds the intervertebral disk region in the extraction results, at an in-between position along the spline curve of the two intervertebral disk regions in the set. Thereafter, the extraction unit applies the Region Growing processing, designating the intervertebral disk region as the seed point, thereby extracting the two-dimensional intervertebral disk region, as explained in the processing performed by the 2D intervertebral-disk-region extraction unit $26c$ in the above embodiment, for each of the intervertebral disk regions including the added intervertebral disk region.

For example, the extraction unit determines whether there is an intervertebral disk region having been extracted excessively based on the positional relation of the extracted intervertebral disk regions, and when there is an intervertebral disk region having been extracted excessively, the extraction unit deletes the intervertebral disk region. Specifically, as explained in the processing performed by the 2D intervertebral-disk-region extraction unit $26c$ in the above embodiment, the extraction unit obtains the two-dimensional spline curve passing through the midpoint of the plurality of lines visualized by the edge enhancement process for each of the difference images in which the spines are visualized, to detect the intervertebral disk region based on the profile of the signal values along the spline curve. Thereafter, the extraction unit obtains a distance between the intervertebral disk regions along the spline curve, for each set of adjacent intervertebral disk regions, for each of the intervertebral disk regions detected on the spline curve. Subsequently, the extraction unit determines whether there is a set of intervertebral disk regions having a considerably smaller distance between the intervertebral disk regions as compared to other sets. When there is the set of intervertebral disk regions having a considerably small distance between the intervertebral disk regions, the extraction unit obtains a distance between an intervertebral disk region in the set and an intervertebral disk region adjacent thereto on the opposite side to the set of intervertebral disk regions, for each of the two intervertebral disk regions in the set. The extraction unit then deletes the intervertebral disk region having the shorter distance of the two intervertebral disk regions from the extraction results. Thereafter, the extraction unit applies the Region Growing processing, designating the intervertebral disk region as the seed point, thereby extracting the two-dimensional intervertebral disk region, as explained in the processing performed by the 2D intervertebral-disk-region extraction unit $26c$ in the above embodiment, for each of the intervertebral disk regions remaining in the extraction results.

In the above embodiment, an example in which the intervertebral disk region is extracted from the entire positioning sagittal image has been explained. However, a part of the positioning sagittal image may be used as a processing object to extract the intervertebral disk region therefrom. In this case, for example, the extraction unit receives an operation to set a range for each of the sagittal images from an operator and extracts the intervertebral disk region from the range set by the operation.

For example, after the imaging control unit $26f$ acquires a plurality of positioning sagittal images, the extraction unit displays one of the imaged positioning sagittal images on the display 25. The extraction unit then receives an operation to specify the range with respect to the positioning sagittal image displayed on the display 25 from an operator via the input device 24. For example, the extraction unit receives an operation to set a rectangular range on the positioning sagittal image. The extraction unit then performs a process of extracting the intervertebral disk region as described above with respect to the range set by the operator as the processing object, for each of the positioning sagittal images.

In the above embodiment, an example in which after the positioning sagittal image is acquired by the imaging control unit $26f$, the intervertebral disk region is automatically extracted from the acquired positioning sagittal image has been explained. That is, in the above embodiment, the extraction unit starts the process of extracting the intervertebral disk region described above, at the time when execution of an imaging protocol for taking a plurality of sagittal images is completed.

Meanwhile, for example, after the imaging protocol for taking the sagittal images is executed, the extraction unit may perform the process of extracting the intervertebral disk region by using the sagittal image selected by an operator. In this case, for example, the extraction unit receives an operation to specify the executed imaging protocol from the operator, and extracts the intervertebral disk region spanning across a plurality of sagittal images based on the sagittal images acquired by the imaging protocol specified by the operation. Accordingly, for example, the operator may select an appropriate sagittal image from the sagittal images already acquired to set the imaging regions of the intervertebral disk image.

In the above embodiment, an example in which the intervertebral disk region is extracted under the same condition has been explained; however, the embodiment is not limited thereto. Generally, the vertebral bones included in the spines are classified into cervical vertebra, thoracic vertebra, lumber vertebra, sacral vertebra, and coccygeal vertebra, and of these, the cervical vertebra, the thoracic vertebra, and the lumber vertebra are formed of a plurality of vertebral bones. It is known that the intervertebral disks have a size, an inclination, and a thickness different from each other in the intervertebral disks included in the cervical vertebra, the thoracic vertebra, and the lumber vertebra. Therefore, for example, the extraction unit may change the extraction conditions related to extraction of the intervertebral disk regions depending on the region to be imaged.

In this case, for example, the extraction unit receives an operation to specify any of the cervical vertebra, the thoracic vertebra, and the lumber vertebra as a region to be imaged from an operator. For example, the extraction unit receives an operation to input a region to be imaged as a part of the imaging conditions via the input device 24. The extraction unit then changes the extraction conditions related to extraction of the intervertebral disk regions depending on the region specified by the operator. For example, the intervertebral disks included in the lumber vertebrae are larger than those included in the cervical vertebrae and the thoracic vertebrae. Therefore, the boundary with the vertebral bodies may be clearly visualized. On the other hand, the intervertebral disks included in the cervical vertebrae are smaller than those included in the thoracic vertebrae and the lumber vertebrae, and thus the boundary with the vertebral bodies is hard to be visualized clearly, and distinguishing from noise is difficult. Therefore, for example, when the region to be imaged is the lumber vertebrae, the extraction unit makes the extraction conditions of the intervertebral disk regions more stringent as compared to a case where the region to be imaged is the cervical vertebrae. For example, when the region to be imaged is the lumber vertebrae, the extraction unit sets a high threshold of signal values for specifying a high signal region as the intervertebral disk region as compared to a case where the region to be imaged is the cervical vertebrae, at the time of detecting the intervertebral disk regions based on the profile of the signal values along the spline curve obtained on a plurality of difference images in which the spines are visualized. On the other hand, when the region to be imaged is the cervical vertebrae, the extraction unit sets a low threshold of the signal values for specifying a high signal region.

Furthermore, it is considered that in the intervertebral disks included, for example, in the spines, an inclination difference between the adjacent intervertebral disks falls within a predetermined angle because of the structure of the spines. Therefore, for example, after having extracted the three-dimensional intervertebral disk region spanning across the plurality of sagittal images, the extraction unit may exclude the intervertebral disk region regarded as noise from the extraction results based on the inclination difference between the adjacent intervertebral disk regions.

In this case, for example, the extraction unit obtains an inclination difference between the intervertebral disk regions for each set of the adjacent intervertebral disk regions, with respect to the extracted intervertebral disk regions, after having extracted the three-dimensional intervertebral disk region. Thereafter, when there is a set of the intervertebral disk regions in which the obtained inclination difference exceeds a predetermined angle range, the extraction unit obtains an inclination difference between an intervertebral disk region in the set and an intervertebral disk region adjacent thereto on the opposite side to the set of intervertebral disk regions. The extraction unit then deletes the intervertebral disk region having a larger inclination difference of the two intervertebral disk regions from the extraction results.

For example, the extraction unit may change the angle range to be compared with the inclination difference between the intervertebral disk regions depending on the region to be imaged. For example, it is known that the thoracic vertebrae curve largely as compared to the lumber vertebrae. Therefore, when the region to be imaged is the thoracic vertebrae, the extraction unit increases the angle range to be compared with the inclination difference between the intervertebral disk regions, as compared to the case where the region to be imaged is the lumber vertebrae. For example, when the region to be imaged is the thoracic vertebrae, the extraction unit sets the angle range to −30 degrees to +30 degrees, and when the region to be imaged is the lumber vertebrae, sets the angle range to −15 degrees to +15 degrees.

Generally, when sagittal images of the lumber vertebrae are to be acquired, the sacral vertebra located below the lumber vertebrae tends to be imaged together. Further, when sagittal images of the cervical vertebrae are to be acquired, generally, the head located above the cervical vertebrae tends to be imaged together. However, the portions of the sacral vertebra and the head are often unnecessary in order to extract the intervertebral disk regions from the sagittal images. Therefore, for example, the extraction unit may exclude at least a part of the positioning sagittal images from an extraction object of the intervertebral disk region depending on the region to be imaged.

In this case, for example, the extraction unit excludes a predetermined region from the extraction object of the intervertebral disk region for each region to be imaged, with regard to each of the sagittal images. For example, when the region to be imaged is the lumber vertebrae, the extraction unit excludes a region having a predetermined size in a lower part of the sagittal image from the processing object. Accordingly, the region in which the sacral vertebra is visualized in the sagittal image may be excluded from the processing object. Further, for example, when the region to be imaged is the lumber vertebrae, the extraction unit excludes a region having a predetermined size in an upper part of the sagittal image from the processing object in an extraction process of the intervertebral disk region. Accordingly, the region in which the head is visualized in the sagittal image may be excluded from the processing object in the extraction process of the intervertebral disk region.

According to the above embodiments, the following method is also disclosed.

A magnetic resonance imaging method comprising:

extracting, based on a plurality of sagittal images at least including an intervertebral disk of a subject, an intervertebral disk region spanning across the plurality of sagittal images from spines visualized in the plurality of sagittal images; and setting an imaging region of an intervertebral disk image based on the intervertebral disk region.

According to at least one of the embodiments described above, in a diagnostic imaging examination in which intervertebral disks are imaged, imaging regions of the intervertebral disks may be easily set.

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance (MR) imaging apparatus comprising:
  a processor; and
  a memory that stores processor-executable non-transitory instructions that, when executed by the processor, cause the processor to:
  create an average image or maximum intensity projection (MIP) image from a plurality of sagittal MR images of different parallel cross sections of a subject;
  create a plurality of difference images either between the created average image and each sagittal MR image from the plurality of sagittal MR images, or between the created MIP image and each sagittal MR image from the plurality of sagittal MR images;
  select a difference image that visualizes a spine of the subject including an intervertebral disk from the plurality of the difference images based on a distribution of signal values of pixels in each difference image;
  extract, based on the selected difference image, a region of the intervertebral disk spanning across the plurality of sagittal MR images from the spine of the subject visualized in the plurality of sagittal MR images;
  set an MR imaging region of interest including the intervertebral disk based on the extracted region of the intervertebral disk; and
  perform MR imaging based on the set MR imaging region of interest.

2. The magnetic resonance imaging apparatus according to claim 1, wherein,
  in extracting the region of the intervertebral disk, the processor extracts two-dimensional regions of the intervertebral disk from the spine of the subject visualized in the plurality of sagittal MR images, and extracts a three-dimensional region of the intervertebral disk spanning across the plurality of sagittal MR images based on the extracted two-dimensional regions of the intervertebral disk, and,
  in setting the MR imaging region, the processor sets the MR imaging region based on the extracted three-dimensional regions of the intervertebral disk.

3. The magnetic resonance imaging apparatus according to claim 2, wherein, in extracting the region of the intervertebral disk, the processor also extracts a plurality of regions of the spine from the plurality of sagittal MR images, and extracts the two-dimensional regions of the intervertebral from the extracted plurality of regions of the spine.

4. The magnetic resonance imaging apparatus according to claim 1, wherein, in setting the MR imaging region, the processor further sets an MR imaging region of a coronal image including the intervertebral disks of a spine of a subject based on the extracted region of the intervertebral disk.

5. The magnetic resonance imaging apparatus according to claim 1, wherein, in setting the MR imaging region, the processor further sets an MR imaging region of a diagnostic sagittal MR image based on the extracted region of the intervertebral disk.

6. The magnetic resonance imaging apparatus according to claim 5, wherein
  the non-transitory instructions, when executed by the processor, further causes the processor to acquire an MR slice image of the MR imaging region as the diagnostic sagittal MR_image based on the set MR imaging region, and,
  in setting the MR imaging region, the processor displays on a display the diagnostic sagittal MR image on which the set MR imaging region includes the intervertebral disk.

7. The magnetic resonance imaging apparatus according to claim 1, wherein, in setting the MR imaging region, the processor sets a plurality of MR imaging regions each including an intervertebral disk, and displays on a display a GUI (Graphical User Interface) that receives an operation from an operator selecting an MR imaging region as an imaging object from the set MR imaging regions.

8. The magnetic resonance imaging apparatus according to claim 7, wherein, in setting the MR imaging region, the processor receives an operation inputting a number of MR imaging regions that are to be selected as the imaging object via the GUI, and then subsequently selects that number of MR imaging regions by using the number that was input by the operator.

9. The magnetic resonance imaging apparatus according to claim 7, wherein, in setting the MR imaging region, the processor receives an operation specifying either one of two directions opposite to each other via the GUI, and then moves the selected MR imaging region as the imaging object, among the set MR imaging regions, in the direction specified by the operator.

10. The magnetic resonance imaging apparatus according to claim 1, wherein, in extracting the region of the intervertebral disk, the processor changes an extraction condition related to extraction of the region of the intervertebral disk depending on the MR imaging region being imaged.

11. The magnetic resonance imaging apparatus according to claim 1, wherein the plurality of sagittal MR images are respectively parallel to a sagittal cross section including intervertebral disks and a spinal canal of the subject.

12. The magnetic resonance imaging apparatus according to claim 1, wherein the plurality of sagittal MR images are acquired respectively according to an MR pulse sequence in which only intervertebral disks having a signal value higher than a vertebral body are imaged during the MR imaging that acquires the plurality of sagittal MR images.

13. The magnetic resonance imaging apparatus according to claim 1, wherein the plurality of sagittal MR images are acquired respectively according to an MR pulse sequence in which protons of water and fat are imaged with a phase of said water and fat protons being shifted from each other during the MR imaging that acquires the plurality of sagittal MR images.

14. The magnetic resonance imaging apparatus according to claim 1, wherein, in extracting the region of the intervertebral disk, the processor extracts a plurality of regions of intervertebral disks, and corrects an extraction result of at least one of the extracted regions intervertebral disks based on a positional relationship of the extracted regions of the intervertebral disks.

15. The magnetic resonance imaging apparatus according to claim 14, wherein, in extracting the region of the intervertebral disk, the processor determines whether there is an intervertebral disk region that has failed to be extracted based on the positional relationship of the extracted regions of the intervertebral disks, and when there is an intervertebral disk that has failed to be extracted, the processor adds a region of the failed intervertebral disk to the extracted regions of the intervertebral disks.

16. The magnetic resonance imaging apparatus according to claim 14, wherein, in extracting the region of the intervertebral disk, the processor determines whether there is an intervertebral disk that has been extracted excessively based on the positional relationship of the extracted regions of the intervertebral disks regions, and when there is an intervertebral disk that has been extracted excessively, the processor deletes a region of the excessively extracted intervertebral disk from the extracted regions of the intervertebral disks.

17. The magnetic resonance imaging apparatus according to claim 1, wherein, in extracting the region of the intervertebral disk, the processor receives an operation that sets a range for each of the plurality of sagittal MR images from an operator, and then extracts the region of the intervertebral disk selected from the range that has been set by the operator.

18. The magnetic resonance imaging apparatus according to claim 1, wherein, in extracting the region of the intervertebral disk, the processor starts a process of extracting the intervertebral disk region at a time of completing an execution of a magnetic resonance imaging protocol in which the plurality of sagittal MR images are acquired.

19. The magnetic resonance imaging apparatus according to claim 1, wherein, in extracting the region of the intervertebral disk, the processor receives an operation specifying a magnetic resonance imaging protocol that has been executed from an operator, and extracts, based on the plurality of sagittal MR images acquired according to the magnetic resonance imaging protocol specified by the operator, the region of the intervertebral disk spanning across the plurality of sagittal MR images.

* * * * *